United States Patent [19]

Olesen

[11] Patent Number: 5,994,373
[45] Date of Patent: Nov. 30, 1999

[54] SUBSTITUTED AZACYCLIC COMPOUNDS

[75] Inventor: Preben Houlberg Olesen, Copenhagen, Denmark

[73] Assignee: Novo Nordisk A/S Novo Alle DK 2880, Bagsvaerd, Denmark

[21] Appl. No.: 08/981,228

[22] PCT Filed: Jun. 28, 1996

[86] PCT No.: PCT/DK96/00291

§ 371 Date: Dec. 19, 1997

§ 102(e) Date: Dec. 19, 1997

[87] PCT Pub. No.: WO97/01555

PCT Pub. Date: Jan. 16, 1997

[30] Foreign Application Priority Data

Jun. 29, 1995 [DK] Denmark .................................. 0755/95

[51] Int. Cl.$^6$ .......................... C07D 413/04; A61K 31/44
[52] U.S. Cl. .......................... 514/340; 514/342; 546/275; 546/280
[58] Field of Search ...................................... 546/275, 280; 514/340, 342

[56] References Cited

U.S. PATENT DOCUMENTS 4,530,927   7/1985   Winters .................................... 514/215

FOREIGN PATENT DOCUMENTS 0 296 721   6/1993   European Pat. Off. .
WO 95/07277   3/1995   WIPO .

*Primary Examiner*—Robert Gerstl
*Attorney, Agent, or Firm*—Steve T. Zelson; Carol E. Rozek

[57] ABSTRACT

The present invention relates to therapeutically active heterocyclic compounds, to methods for their preparation and to pharmaceutical compositions comprising the compounds. The novel compounds are useful in treating diseases in the central nervous system related to malfunctioning of the nicotinic cholinergic system.

13 Claims, No Drawings

SUBSTITUTED AZACYCLIC COMPOUNDS

CROSS-REFERENCE TO RELATED APPLICATIONS

This application is a 35 U.S.C. 371 national application of PCT/DK96/00291 filed Jun. 28, 1996 and claims priority under 35 U.S.C. 119 of Danish application 0755/95 Filed Jun. 29, 1995, the contents of which are fully incorporated herein by reference.

1. Field of the Invention

The present invention relates to heterocyclic compounds which are cholinergic ligands selective for neuronal nicotinic channel receptors, to methods for their preparation, to pharmaceutical compositions comprising them, and to their use in treating cognitive, neurological and mental disorders, which are characterized by decreased cholinergic function. The invention also relates to a method of treating Parkinson's disease by modulating the process of dopamine secretion, a method of treating or preventing withdrawal symptoms caused by cessation of chronic or long term use of tobacco products, as well as a method for treating obesity.

2. Background of the Invention

Nicotinic and muscarinic receptors are the two distinct types of cholinergic receptors named after their selectivity for muscarine and nicotine, respectively. The cholinergic system is the neurotransmitter system that best correlates with memory and cognitive functions. Traditionally, the cholinergic hypothesis for senile dementia of the Alzheimer type (SDAT) has focused on muscarinic acetylcholine receptors (mAChR), and only recently an interest in the role of the nicotinic acetylcholine receptors (nAChR) in SDAT has emerged. This interest was spurred by the relatively recent discovery that nAChR are not only located on the skeletal muscle but also in the brain.

It has been shown that the number of nAChR was decreased in SDAT patients (Nordberg et al. J. Neurosci. Res.Vol. 31, pp. 103–111 (1992); Giacobini Advances in Experimental Medicine and Biology, Vol. 296, pp.9205–9295, (1993); Schroeder et al., Neurobiol. of Aging, Vol. 12, pp. 259–262, (1991); Whitehouse et al., Neurology, Vol. 38, pp. 720–723, (1988); Flynn and Mash, J. Neurochem., Vol. 47, pp. 8702—8702, (1993)). Similar deficiencies in choline acetyltransferase activity and acetylcholine synthesis suggest that presynaptic receptors on cholinergic nerve terminals are preferentially lost in SDAT (Nordberg, J. Reprod. Fert. Suppl., Vol 46, pp. 145–154, (1993)). Therefore, it has been assumed that the loss of nAChR may correlate with age related onset of disorders of memory and cognitive functions, and that nicotinic replacement therapy may prove beneficial in SDAT. Indeed nicotine improved attention and memory in healthy humans (Warburton, Prog. Neuro. Psychopharmacol. Biol. Psychiatry, Vol. 16, pp. 181–191, (1992)) as well as in Alzheimer's disease patients, (Jones et al. Psychopharmacology, Vol. 108, pp. 485–494, (1992); Gitelman and Prohovnik, Neurobiol. of Aging, Vol. 13, pp. 313–318, (1992); Newhouse et al., Psychopharmacology, Vol. 95, pp. 171–175, (1988); Sahakian et al., Br. J. Psychiatry, Vol.154, pp. 9004–904, (1993)). Further the nicotinic antagonist mecamylamine has been shown to cause cognitive impairment in an age related way, (Newhouse et al., Neuropsychopharmacology, Vol 10, pp. 93–107, (1 994)). p Parkinson's disease (PD) is a debilitating neurodegenerative disease, presently of unknown etiology, characterized by tremors and muscular rigidity. There is evidence that nicotine may also have beneficial effects in PD. Studies show that smoking may protect against the development of PD, (Ishikawa and Mmiyatake, J. Neurol. Sci., Vol. 117, pp. 28–32, (1993); Godwin-Austen et al., J. Neurol. Neurosurg. Psychiat., Vol. 45, pp. 577–581, (1982); Reavill, in Nicotine psychopharmacology: Molecular, cellular and behavioral aspects, pp. 307–340, Oxford University Press, (1990)), and that chronic nicotine may protect against cell loss in the substantia nigra caused by lesioning (Janson and Moller, Neuroscience, Vol. 57, 931–941, (1993)). Nicotine has also shown beneficial effects in Tourette's syndrome (Sanberg et al., Biomed. Phamacother., Vol. 43, pp. 19–23, (1989)). Alleviation of negative psychotic symptoms, known as the hypofrontality syndrome in schizophrenia, by nicotinic agonists, have been suggested by data showing that nicotine stimulates dopamine release in the nucleus accumbens more potently than in striatum, (Rowell et al. J. Neurochem., Vol. 49, pp. 1449–1454, (1987); Giorguieff-Chesselet et al., Life Sciences, Vol. 25, pp. 1257–1262, (1 979)), by nicotinic reversal of inactivation of prefrontal neurons (Svenson et al., In the Biology of Nicotine dependence., pp. 169–185, New York, (1990)), and by the observation that nicotine will potentiate dopaminergic effects in various behavioral models, (Reavill, in Nicotine psychopharmacology: Molecular, cellular and behavioral aspects, pp. 307–340, Oxford University Press, (1990); Rosecrans et al., Psychopharmacol. Commmun., Vol. 2, pp. 349–356, (1976); Reavill and Stolerman, J. Psychopharmacol., Vol. 1, pp. 264, (1987)).

In recent years there have been several studies on the effects of nicotine and food consumption and associated changes in body weight in rat and human. (Greenberg et al., Addictive behaviours, Vol. 7, pp. 317–331, (1982) and Greenberg et al., Psychopharmacology, Vol. 90, pp. 101–105, (1984)). The appetite effects of nicotine have been suggested to be mediated via modulation of CCK peptides in the paraventricular hypothalamic nucleus (Fuxe et al., Acta Physiologica Scandinavica, Vol. 125, pp. 437–443, (1985)).

DESCRIPTION OF THE INVENTION

It is an object of the invention to provide compounds with affinity and selectivity for nicotinic cholinergic receptors, to methods for their preparation, to pharmaceutical compositions containing them, and to their use in treating Alzheimer's disease, Parkinson's disease, Tourette's syndrome, ulcerative colitis, obesity, other central nervous system and gastrointestinal disorders as well as severe pain.

The present invention relates to novel substituted azacyclic compounds of formula I selected from the following:

(I)

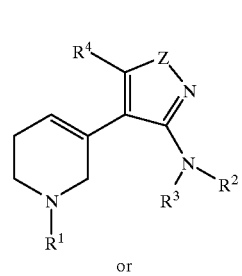

or

-continued

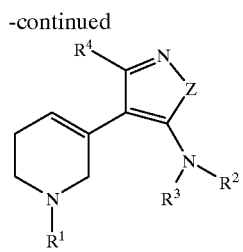

wherein
- Z is oxygen or sulphur; and
- $R^1$ is hydrogen, $C_{1-3}$-alkyl, $C_{2-4}$-alkenyl, $C_{2-4}$-alkynyl or $C_{3-4}$-cycloalkyl or benzyl; and
- $R^2$ and $R^3$ independently are hydrogen, $C_{1-6}$-alkyl optionally substituted with one, two or three fluorine atoms or cyano, $C_{2-6}$-alkenyl optionally substituted with one, two or three fluorine atoms, $C_{2-6}$-alkynyl optionally substituted with one, two or three fluorine atoms, $C_{3-7}$-cycloalkyl, phenyl or benzyl wherein each aromatic group is optionally substituted with halogen, $C_{1-4}$-alkyl, —$NO_2$, —CN, —$CF_3$ or —$OR^6$ wherein $R^6$ is hydrogen, $C_{1-3}$-alkyl, $C_{2-4}$-alkenyl, $C_{2-4}$-alkynyl or $C_{3-4}$-cycloalkyl, or $R^2$ and $R^3$ form together with the nitrogen atom a three, four, five, six or seven membered saturated or unsaturated heterocyclic ring; and
- $R^4$ is hydrogen, halogen, $C_{1-6}$-alkyl optionally substituted by one, two or three fluorine atoms, $C_{2-6}$-alkenyl optionally substituted by one, two or three fluorine atoms, $C_{2-6}$-alkynyl optionally substituted by one, two or three fluorine atoms, $C_{3-7}$-cycloalkyl, —$OR^5$ or —$SR^5$ wherein $R^5$ is $C_{1-6}$-alkyl, $C_{2-6}$-alkenyl or $C_{2-6}$-alkynyl each of which is optionally substituted with one, two or three fluorine atoms; or a pharmaceutically acceptable salt thereof.

Examples of pharmaceutically acceptable salts include inorganic and organic acid addition salts such as hydrochloride, hydrobromide, sulphate, phosphate, acetate, fumarate, maleate, citrate, lactate, tartrate, oxalate, or similar pharmaceutically-acceptable inorganic or organic acid addition salts, and include the pharmaceutically acceptable salts listed in Journal of Pharmaceutical Science, 66, 2 (1977) which are hereby incorporated by reference.

The compounds of formula I may exist as geometric and optical isomers and all isomers and mixtures thereof are included herein. Isomers may be separated by means of standard methods such as chromatographic techniques or fractional crystallization of suitable salts.

Alkyl, alkenyl and alkynyl as used herein mean straight or branched alkyl, alkenyl or alkynyl chains.

In a preferred embodiment the compounds of the invention have the formula Ib

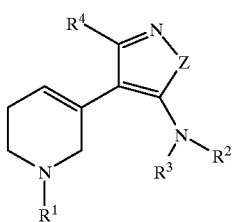

(Ib)

wherein Z, $R^1$, $R^2$, $R^3$ and $R^4$ have the meanings defined above.

The invention also relates to a method of preparing the above mentioned compounds of formula I. These methods comprise:

a) reacting a compound of formula II

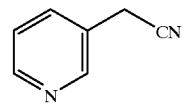

(II)

with a compound of formula III

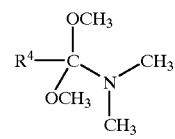

(III)

wherein $R^4$ has the meaning defined above, which formed compound is reacted with hydroxylamine to give a compound of formula IV

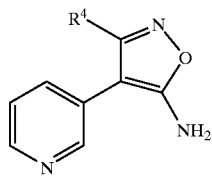

(IV)

wherein $R^4$ has the meaning defined above, which formed compound is quaternized with $R^1$—Hal and subsequently reduced with sodium borohydride to form a compound of formula V

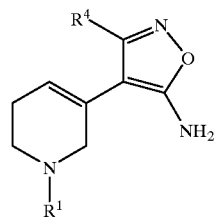

(V)

wherein $R^1$ and $R^4$ have the meanings defined above, which formed compound can be stepwise alkylated with first $R^2$—Hal and then $R^3$—Hal to give a compound of formula VI

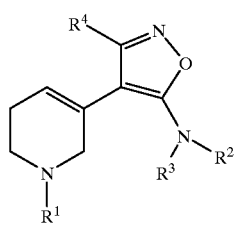

(VI)

wherein $R^1$, $R^2$, $R^3$ and $R^4$ have the meanings defined above;
or
b) a compound of formula IV

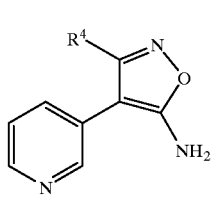

(IV)

wherein $R^4$ has the meaning defined above is stepwise alkylated with first $R^2$—Hal and then $R^3$—Hal to give a compound of formula VII

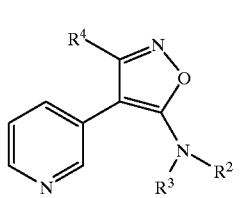

(VII)

wherein $R^2$, $R^3$ and $R^4$ have the meanings defined above, which formed compound is quaternized with $R^1$—Hal and subsequently reduced with sodium borohydride to give a compound of formula VI wherein $R^1$, $R^2$, $R^3$ and $R^4$ have the meanings defined above.

The pharmacological properties of the compounds of the invention can be illustrated by determining their capability to inhibit the specific binding of $^3$H-methylcarbamylcholine ($^3$H-MCC) (Abood and Grassi, Biochem. Pharmacol., Vol. 35, pp. 4199–4202, (1986)).

$^3$H-MCC labels the nicotinic receptors in the CNS. The inhibitory effect on $^3$H-MCC binding reflects the affinity for nicotinic acetylcholine receptors.

Fresh or frozen rat, brain tissue (hippocampus or cortex) was homogenized in assay buffer (50 mM Tris-HCl, pH 7.4, 120 mM NaCl, 5 mM KCl, 2 mM $CaCl_2$, 1 mM $MgCl_2$) and centrifuged for 10 min. at 40.000×g. Pellets were subsequently reconstituted in assay buffer and an appropriate amount of tissue sample was mixed in tubes with $^3$H-methylcarbamylcholine (NEN, NET-951; final concentration 2 nM) and test drug. The tubes were incubated at 0° C. for 60 min. Unbound ligand was separated from bound ligand by vacuum filtration through GF/B filters presoaked in 0.5 % polyethylenimine. Filters were washed three times with 5 ml wash buffer (50 mM Tris-HCl, pH 7.4) and transferred to vials. 4 ml scintillation fluid was added and the radioactivity was measured by scintillation counting. Unspecific binding was measured with 10 $\mu$M nicotine.

The $IC_{50}$ values of the test compounds were determined by nonlinear regression analyses (GraphPad InPlot).

Furthermore, the pharmacological properties of the compounds of the invention can also be illustrated by determining their capability to inhibit the specific binding of $^3$H-Oxotremorine-M ($^3$H-Oxo). Birdsdall N. J. M., Hulme E. C., and Burgen A. S. V. (1980). "The Character of Muscarinic Receptors in Different Regions of the Rat Brain". Proc. Roy. Soc. London (Series B) 207,1.

$^3$H-Oxo labels muscarinic receptor in the CNS (with a preference for agonist domains of the receptors). Three different sites are labelled by $^3$H-Oxo. These sites have affinity of 1.8, 20 and 3000 nM, respectively. Using the present experimental conditions only the high and medium affinity sites are determined.

The inhibitory effects of compounds on $^3$H-Oxo binding reflects the affinity for muscarinic acetylcholine receptors.

All preparations are performed at 0–4° C. unless otherwise indicated. Fresh cortex (0.1–1 g) from male Wistar rats (150–250 g) is homogenized for 5–10 s in 10 ml 20 mM Hepes pH: 7.4, with an Ultra-Turrax homogenizer. The homogenizer is rinsed with 10 ml of buffer and the combined suspension centrifuged for 15 min. at 40,000×g. The pellet is washed three times with buffer. In each step the pellet is homogenized as before in 2×10 ml of buffer and centrifuged for 10 min. at 40,000×g.

The final pellet is homogenized in 20 mM Hepes pH: 7.4 (100 ml per g of original tissue) and used for binding assay. Aliquots of 0.5 ml is added 25 $\mu$l of test solution and 25 $\mu$l of $^3$H-Oxotremorine (1.0 nM, final concentration) mixed and incubated for 30 min. at 25° C. Non-specific binding is determined in triplicate using arecoline (1 $\mu$g/ml, final concentration) as the test substance. After incubation samples are added 5 ml of ice-cold buffer and poured directly onto Whatman GF/C glass fiber filters under suction and immediately washed 2 times with 5 ml of ice-cold buffer. The amount of radioactivity on the filters are determined by conventional liquid scintillation counting. Specific binding is total binding minus non specific binding.

Test substances are dissolved in 10 ml water (if necessary heated on a steam-bath for less than 5 min.) at a concentration of 2.2 mg/ml. 25–75% inhibition of specific binding must be obtained before calculation of $IC_{50}$. The test value will be given as $IC_{50}$ (the concentration (nM) of the test substance which inhibits the specific binding of $^3$H-Oxo by 50%).

$IC_{50}$=(applied test substance concentration)×$(C_x/C_o-C_x)$nM where $C_o$ is specific binding in control assays and $C_x$ is the specific binding in the test assay. (The calculations assume normal mass-action kinetics).

Table I illustrates the affinity of the compounds of the present invention for nicotinic and muscarinic receptors as determined by $^3$H-MCC and $^3$H-Oxo binding to rat cortical receptors. The compounds, however, show selective affinity for nicotinic receptors as compared to muscarinic receptors, i.e OXO/MCC>1.

TABLE 1

| Compound | $^3$H-MCC $IC_{50}$ nM | $^3$H-Oxo $IC_{50}$ nM | Oxo/ MCC Ratio |
|---|---|---|---|
| 3 | 230 | 4400 | 19 |
| 5 | 62 | 1400 | 23 |
| 7 | 40 | 5200 | 130 |
| 14 | 85 | 4000 | 47 |

The compounds of the invention are effective over a wide dosage range. For example, in the treatment of adult humans, dosages from about 0.05 to about 100 mg, preferably from about 0.1 to about 100 mg, per day may be used. A most preferable dosage is about 10 mg to about 70 mg per day. In choosing a regimen for patients suffering from diseases in the central nervous system caused by malfunctioning of the nicotinic cholinergic system it may frequently be necessary to begin with a dosage of from about 30 to about 70 mg per day and when the condition is under control to reduce the dosage as low as from about 1 to about 10 mg per day. The exact dosage will depend upon the mode of administration, form in which administered, the subject to be treated and the body weight of the subject to be treated, and the preference and experience of the physician or veterinarian in charge.

The route of administration may be any route, which effectively transports the active compound to the appropriate or desired site of action, such as oral or parenteral e.g. rectal, transdermal, subcutaneous, intravenous, intraurethral, intramuscular, topical, intranasal, ophthalmic solution or an ointment, the oral route being preferred.

Typical compositions include a compound of formula I or a pharmaceutically acceptable acid addition salt thereof, associated with a pharmaceutically acceptable carrier. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, the compounds are dispensed in unit form comprising from about 1 to about 100 mg in a pharmaceutically acceptable carrier per unit dosage.

A typical tablet, appropriate for use in this method, may be prepared by conventional tabletting techniques and contains:

| | |
|---|---|
| Active compound | 5.0 mg |
| Lactosum | 67.8 mg Ph. Eur. |
| Avicel ® | 31.4 mg |
| Amberlite ® | 1.0 mg |
| Magnesii stearas | 0.25 mg Ph. Eur. |

The invention will now be described in further detail with reference to the following examples:

EXAMPLE 1

α-(Dimethylamino)-α-(3-pyridyl)acetonitrile 1-(3-Pyridyl)acetonitrile (5.9 g, 50 mmol) was dissolved in DMFDMA (10 ml) and stirred at 100° C. for 0.5 hour. After cooling to room temperature diethyl ether was added and the title compound was filtered. Yield 8.2 g.

3-(5-Amino-4-isoxazolyl)pyridine

To a solution of α-(dimethylamino)-α-(3-pyridyl)acetonitrile (5.19 g, 30 mmol) in acetic acid (40 ml) was added hydroxylamine hydrochloride (2.8 g, 40 mmol). The reaction mixture was stirred at 100° C. for 1 hour, cooled to room temperature and concentrated in vacuo. Water (50 ml) was added and the reaction mixture neutralized with solid potassium carbonate. The precipitated compound was filtered washed with water and dried giving the title compound in 4.2 g yield.

3-(5-Amino-4-isoxazolyl)-1,2,5,6-tetrahydro-1-methylpyridine oxalate

To a solution of 3-(5-amino-4-isoxazolyl)pyridine (1.0 g, 6.25 mmol) in acetone (25 ml) was added iodomethane (2 ml). The reaction mixture was stirred overnight at room temperature, then evaporated in vacuo. The solid compound was dissolved in methanol (30 ml) and reduced by adding sodium borohydride (0.5 g, 13.5 mmol) in small portions. The reaction mixture was concentrated in vacuo and water (40 ml) was added. The water phase was extracted with ether (4×30 ml). The combined ether extracts were dried and evaporated. The crude compound was crystallized as the oxalate salt from acetone to give the title compound in 0.6 g yield. M.p. 138–139° C. (Compound 1).

In exactly the same manner the following compounds were prepared:

3-(5-amino-4-isoxazolyl)-1,2,5,6-tetrahydro-1-ethylpyridine oxalate, starting from 3-(5-amino-4-isoxazolyl)pyridine and iodoethane (Compound 19). Mp. 112–113° C.; 3-(5-amino-4-isoxazolyl)-1,2,5,6-tetrahydro-1-benzylpyridine oxalate, starting from 3-(5-amino-4-isoxazolyl)pyridine and benzylbromide (Compound 20). Mp. 130–131° C.

3-(5-Dimethylamino-4-isoxazolyl)-1,2,5,6-tetrahydro-1-methylpyridine oxalate and 3-(5-methylamino-4-isoxazolyl)-1,2,5,6-tetrahydro-1-methylpyridine oxalate To a solution of 3-(5-amino-4-isoxazolyl)pyridine (1.6 g, 10 mmol) in DMF (20 ml) was added powdered potassium hydroxide (1.0 g). The reaction mixture was stirred at room temperature for 5 min. and iodomethane (1.5 g, 12 mmol) was added. The reaction mixture was stirred for 5 min. at room temperature and water was added. The water phase was extracted with ether (3×50 ml). The combined extracts were dried and evaporated in vacuo. The residue was dissolved in acetone (30 ml) and iodomethane (2 ml, 32 mmol) was added. After stirring overnight the reaction mixture was concentrated in vacuo. The residue was dissolved in methanol (30 ml) and reduced by adding sodium borohydride (720 mg, 20 mmol) in small portions at 0° C. The mixture was evaporated and water (50 ml) was added. The water phase was extracted with ethyl acetate (4×30 ml). The combined organic phases were dried and evaporated. The crude compound was purified by column chromatography (SiO$_2$; eluent: CH$_2$Cl$_2$/MeOH: 9/1). The first fractions contained 3-(5-dimethylamino-4-isoxazolyl)-1,2,5,6-tetrahydro-1-methylpyridine. The free base was crystallised as the oxalate salt giving the title compound in 500 mg yield. M.p. 106–107° C. (Compound 2). The later fractions contained 3-(5-methylamino-4-isoxazolyl)-1,2,5,6-tetrahydro-1-metylpyridine. The free base was crystallized as the oxalate salt giving the title compound in 1.0 g yield. M.p. 149–150° C. (Compound 3).

In exactly the same manner the following compounds were prepared:

3-(5-Diethylamino-4-isoxazolyl)-1,2,5,6-tetrahydro-1-methylpyridine oxalate, M.p. 128–129° C., (Compound 4) and 3-(5-ethylamino-4-isoxazolyl)-1,2,5,6-tetrahydro-1-methylpyridine oxalate, M.p. 132–133° C., (Compound 5) both from 3-(5-amino-4-isoxazolyl)pyridine and iodoethane.

3-(5-Dipropylamino-4-isoxazolyl)-1,2,5,6-tetrahydro-1-methylpyridine oxalate, M.p. 123–124° C., (Compound 6), and 3-(5-propylamino-4-isoxazolyl)-1,2,5,6-tetrahydro-1-metylpyridine oxalate, M.p. 136–137° C., (Compound 7) both from 3-(5-amino-4-isoxazolyl)pyridine and iodopropane.

3-(5-Dibutylamino-4-isoxazolyl)-1,2,5,6-tetrahydro-1-methylpyridine oxalate, M.p. 146–148° C., (Compound 8) from 3-(5-amino-4-isoxazolyl)-pyridine and iodobutane.

3-(5-Piperidinyl-4-isoxazolyl)-1,2,5,6-tetrahydro-1-methylpyridine oxalate, M.p. 138–140° C., (Compound 9) from 3-(5-amino-4-isoxazolyl)pyridine and 1,5-dibromopentane.

EXAMPLE 4

3-(5-Amino-3-methyl-4-isoxazolyl)pyridine

A solution of 3-pyridylacetonitrile (2.0 g, 17 mmol) in DMADMA (3 ml) was stirred at 100° C. for 0.5 hour. The reaction mixture was evaporated in vacuo. The residue was dissolved in acetic acid (30 ml) and hydroxylamine hydrochloride (2.8 g, 40 mmol) was added. The reaction mixture was stirred at 100° C. for 1 hour, cooled to room temperature and evaporated in vacuo. Water (30 ml) was added to the residue and the reaction mixture was neutralized with solid potassium carbonate. The precipitated compound was filtered, washed with water and dried. Yield 1.8 g.

3-(5-Amino-3-methyl-4-isoxazolyl)-1,2,5,6-tetrahydropyridine oxalate

To a solution of 3-(5-amino-3-methyl-4-isoxazolyl) pyridine (0.9 g, 5 mmol) in a mixture of methanol (15 ml) and acetone (15 ml) was added iodomethane (2 ml, 32 mmol). The reaction mixture was stirred overnight at room temperature, then evaporated in vacuo. The solid material obtained was dissolved in methanol (40 ml) and reduced by adding sodium borohydride (0.5 g, 113.5 mmol) in small portions. The reaction mixture was concentrated in vacuo and water (40 ml) was added. The water phase was extracted with ethyl acetate (5×20 ml). The combined organic phases were dried and evaporated in vacuo. The crude compound was crystallized with oxalic acid from acetone in 800 mg yield (56%). M.p. 189–190° C. (Compound 10).

EXAMPLE 5

3-(5-Propylamino-4-isoxazolyl)-1,2,5,6-tetrahydro-1-methylpyridine oxalate

To a solution of 3-(5-amino-4-isoxazolyl)-1,2,5,6-tetrahydro-1-methylpyridine (1.5 g, 8.3 mmol) in dimethylformamide (25 ml) was added powdered potassium hydroxide (1.14 g, 20 mmol). The reaction mixture was stirred at room temperature for 1 min. 1-Iodopropane (1.41 g, 8.3 mmol) was added and the reaction mixture was stirred for 1 min. The reaction mixture was acidified with a 1 N hydrochloric acid solution. The water phase was extracted with ether (2×30 ml), then made alkaline with ammonium hydroxide (25% in water) and extracted with methylene chloride (3×30 ml). The combined alkaline extracts were dried over magnesium sulfate and evaporated. The residue was purified by column chromatography (SiO$_2$; eluent: CH$_2$Cl$_2$/MeOH: 9/1). The free base was crystallized with oxalic acid in acetone giving the title compound in 450 mg yield. (Compound 7).

In exactly the same manner the following compounds were prepared:

3-(5-Methylamino-4-isoxazolyl)-1,2,5,6-tetrahydro-1-methylpyridine oxalate from 3-(5-amino-4-isoxazolyl)-1,2,5,6-tetrahydro-1-methylpyridine and iodomethane. (Compound 3).

3-(5-Ethylamino-4-isoxazolyl)-1,2,5,6-tetrahydro-1-methylpyridine oxalate from 3-(5-amino-4-isoxazolyl)-1,2,5,6-tetrahydro-1-methylpyridine and iodoethane. (Compound 5).

3-(5-Butylamino-4-isoxazolyl)-1,2,5,6-tetrahydro-1-methylpyridine oxalate from 3-(5-amino-4-isoxazolyl)-1,2,5,6-tetrahydro-1-methylpyridine and 1-iodobutane. M.p. 125–126° C. (Compound 11).

3-(5-Pentylamino-4-isoxazolyl)-1,2,5,6-tetrahydro-1-methylpyridine oxalate from 3-(5-amino-4-isoxazolyl)-1,2,5,6-tetrahydro-1-methylpyridine and 1-iodopentane. M.p. 99–100° C. (Compound 12).

3-(5-Hexylamino-4-isoxazolyl)-1,2,5,6-tetrahydro-1-methylpyridine oxalate from 3-(5-amino-4-isoxazolyl)-1,2,5,6-tetrahydro-1-methylpyridine and 1-iodohexane. M.p. 92–93° C. (Compound 13).

3-(5-Benzylamino-4-isoxazolyl)-1,2,5,6-tetrahydro-1-methylpyridine oxalate from 3-(5-amino-4-isoxazolyl)-1,2,5,6-tetrahydro-1-methylpyridine and benzylbromide. M.p. 110–112° C. (Compound 14).

3-(5-Cyanomethylamino-4-isoxazolyl)-1,2,5,6-tetrahydro-1-methylpyridine oxalate from 3-(5-amino-4-isoxazolyl)-1,2,5,6-tetrahydro-1-methylpyridine and chloroacetonitrile. M.p. 149–150° C. (Compound 15).

3-(5-(2-Cyanoethyl)amino-4-isoxazolyl)-1,2,5,6-tetrahydro-1-methylpyridine oxalate from 3-(5-amino-4-isoxazolyl)-1,2,5,6-tetrahydro-1-methylpyridine and 2-bromopropionitrile. M.p. 142–143° C. (Compound 16).

3-(5-propylamino-4-isoxazolyl)-1,2,5,6-tetrahydro-1-ethylpyridine oxalate from 3-(5-amino-4-isoxazolyl)-1,2,5,6-tetrahydro-1-ethylpyridine and iodopropane. M.p. 150–151° C. (Compound 21).

EXAMPLE 6

3-(5-Butylamino-3-methyl-4-isoxazolyl)-1,2,5,6-tetrahydro-1-methylpyridine oxalate To a solution of 3-(5-amino-3-methyl-4-isoxazolyl)-1,2,5,6-tetrahydro-1-methylpyridine (0.39 g, 2.0 mmol) in dimethylformamide (25 ml) was added powdered potassium hydroxide (0.3 g, 5 mmol). The reaction mixture was stirred at room temperature for 1 min. 1-Iodobutane (0.25 ml, 2.1 mmol) was added and the reaction mixture was stirred for 1 min. The reaction mixture was acidified with a 1 N hydrochloric acid solution. The water phase was extracted with ether (2×30 ml), then made alkaline with ammonium hydroxide (25% in water) and extracted with methylene chloride (3×30 ml). The combined alkaline extracts were dried over magnesium sulfate and evaporated. The residue was purified by column chromatography (SiO$_2$; eluent: CH$_2$Cl$_2$/MeOH: 9/1). The free base was crystallized with oxalic acid in acetone giving the title compound in 60 mg yield. M.p. 116–117° C. (Compound 17).

In exactly the same manner the following compound was made:

3-(5-Ethylamino-3-methyl-4-isoxazolyl)-1,2,5,6-tetrahydro-1-methylpyridine oxalate from 3-(5-amino-3-methyl-4-isoxazolyl)-1,2,5,6-tetrahydro-1-methylpyridine and iodoethane. M.p. 128–129° C. (Compound 18).

We claim:
1. A compound of formula I

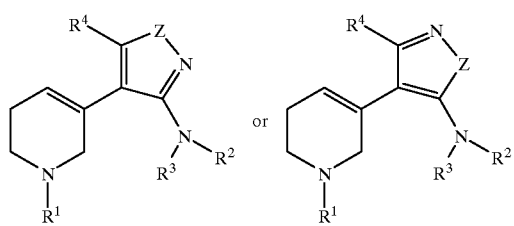

wherein

Z is oxygen or sulphur; and

R$^1$ is hydrogen, C$_{1-3}$-alkyl, C$_{2-4}$-alkenyl, C$_{2-4}$-alkynyl or C$_{3-4}$-cycloalkyl or benzyl; and R$^2$ and R$^3$ independently are C$_{1-6}$-alkyl optionally substituted with one, two or three fluorine atoms or cyano, C$_{2-6}$-alkenyl optionally substituted with one, two or three fluorine atoms, C$_{2-6}$-alkynyl optionally substituted with one, two or three fluorine atoms, C$_{3-7}$-cycloalkyl, phenyl or benzyl wherein each aromatic group is optionally substituted with halogen, C$_{1-4}$-alkyl, —NO$_2$, —CN, —CF$_3$ or —OR$^6$ wherein R$^6$ is hydrogen, C$_{1-3}$-alkyl, C$_{2-4}$-alkenyl, C$_{2-4}$-alkynyl or C$_{3-4}$-cycloalkyl, or R$^2$ and R$^3$ form together with the nitrogen atom a three, four, five, six or seven membered saturated or unsaturated heterocyclic ring; and R$^4$ is hydrogen, halogen, C$_{1-6}$-alkyl optionally substituted by one, two or three fluorine atoms, C$_{2-6}$-alkenyl optionally substituted by one, two or three fluorine atoms, C$_{2-6}$-alkynyl optionally substituted by one, two or three fluorine atoms, C$_{3-7}$-cycloalkyl, —OR$^5$ or —SR$^5$ wherein R$^5$ is C$_{1-6}$-alkyl, C$_{2-6}$-alkenyl or C$_{2-6}$-alkynyl each of which optionally substituted with one, two or three fluorine atoms; or a pharmaceutically acceptable salt thereof.

2. A compound according to claim 1 having the formula Ib

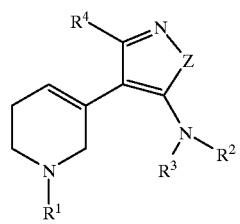

wherein Z, R$^1$, R$^2$, R$^3$ and R$^4$ have the meanings defined above; or a pharmaceutically acceptable salt thereof.

3. A compound according to claim 1 selected from the following:

3-(5-Dimethylamino-4-isoxazolyl)-1,2,5,6-tetrahydro-1-methylpyridine, 3-(5-Methylamino-4-isoxazolyl)-1,2,5,6-tetrahydro-1-methylpyridine, 3-(5-Diethylamino-4-isoxazolyl)-1,2,5,6-tetrahydro-1-methylpyridine, 3-(5-Ethylamino-4-isoxazolyl)-1,2,5,6-tetrahydro-1-methylpyridine, 3-(5-Dipropylamino-4-isoxazolyl)-1,2,5,6-tetrahydro-1-methylpyridine, 3-(5-Propylamino-4-isoxazolyl)-1,2,5,6-tetrahydro-1-methylpyridine, 3-(5-Dibutylamino-4-isoxazolyl)-1,2,5,6-tetrahydro-1-methylpyridine, 3-(5-Piperidinyl-4-isoxazolyl)-1,2,5,6-tetrahydro-1-methylpyridine, 3-(5-Butylamino-4-isoxazolyl)-1,2,5,6-tetrahydro-1-methylpyridine, 3-(5-Pentylamino-4-isoxazolyl)-1,2,5,6-tetrahydro-1-methylpyridine, 3-(5-Hexylamino4-isoxazolyl)-1,2,5,6-tetrahydro-1-methylpyridine, 3-(5-Benzylamino-4-isoxazolyl)-1,2,5,6-tetrahydro-1-methylpyridine, 3-(5-Cyanomethylamino-4-isoxazolyl)-1,2,5,6-tetrahydro-1-methylpyridine, 3-(5-(2-Cyanoethyl)amino-4-isoxazolyl)-1,2,5,6-tetrahydro-1-methylpyridine, 3-(5-Butylamino-3-methyl-4-isoxazolyl)-1,2,5,6-tetrahydro-1-methylpyridine, 3-(5-Ethylamino-3-methyl-4-isoxazolyl)-1,2,5,6-tetrahydro-1-methylpyridine;

or a pharmaceutically acceptable salt thereof.

4. A method of preparing a compound according to claim 1, comprising a) reacting a compound of formula II

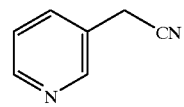

with a compound of formula III

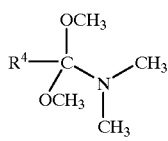
(III)

wherein R⁴ has the meaning defined above, which formed compound is reacted with hydroxylamine to give a compound of formula IV

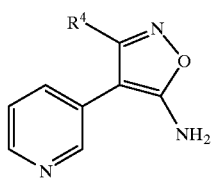
(IV)

wherein R⁴ has the meaning defined above, which formed compound is quaternized with R¹—Hal and subsequently reduced with sodium borohydride to form a compound of formula V

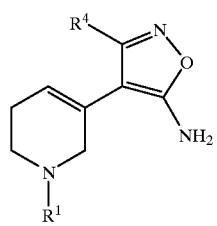
(V)

wherein R¹ and R⁴ have the meanings defined above, which formed compound can be stepwise alkylated with first R²—Hal and then R³—Hal to give a compound of formula VI

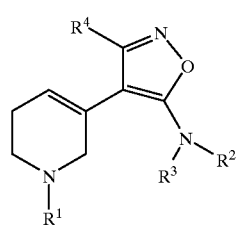
(VI)

wherein R¹, R², R³ and R⁴ have the meanings defined above; or b) a compound of formula IV

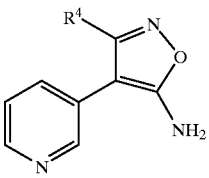
(IV)

wherein R⁴ has the meaning defined above is stepwise alkylated with first R²—Hal and then R³—Hal to give a compound of formula VII

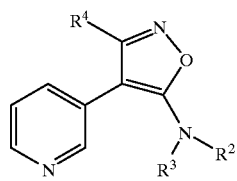
(VII)

wherein R², R³ and R⁴ have the meanings defined above, which formed compound is quaternized with R¹—Hal and subsequently reduced with sodium borohydride to give a compound of formula VI wherein R¹, R², R³ and R⁴ have the meanings defined above.

5. A pharmaceutical composition comprising as active component a compound according to claim 1 together with a pharmaceutically acceptable carrier or diluent.

6. The pharmaceutical composition according to claim 5 in the form of an oral dosage unit or parenteral dosage unit.

7. The pharmaceutical composition according to claim 6, wherein said dosage unit comprises from about 1 to about 100 mg of the compound according to any of claims 1 to 3.

8. A compound according to claim 1 for treating a central nervous system ailment related to malfunctioning of the nicotinic cholinergic system.

9. A compound according to claim 1 for treating Alzheimer's disease, Parkinson's disease, Tourette's syndrome, ulcerative colitis, obesity, gastrointestinal disorders or severe pain, or for treating or preventing withdrawal symptoms caused by cessation of chronic or long term use of tobacco products.

10. A method of treating a central nervous system ailment related to malfunctioning of the nicotinic cholinergic system in a subject in need of such treatment comprising administering to said subject an effective amount of a compound according to claim 1.

11. A method of treating Alzheimer's disease, Parkinson's disease, Tourette's syndrome, ulcerative colitis, obesity, gastrointestinal disorders or severe pain, in a subject in need of such treatment comprising administering to said subject an effective amount of a compound according to claim 1.

12. A method of treating or preventing withdrawal symptoms caused by cessation of chronic or long term use of tobacco products comprising administering to a subject in need thereof an effective amount of a compound according to claim 1.

13. A compound of formula I

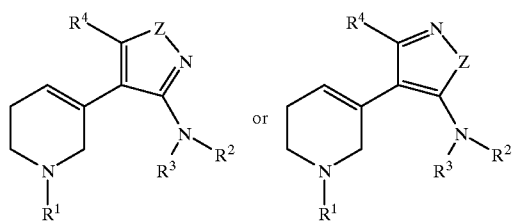

wherein

Z is oxygen or sulphur; and $R^1$ is hydrogen, $C_{1-3}$-alkyl, $C_{2-4}$-alkenyl, $C_{2-4}$-alkynyl or $C_{3-4}$-cycloalkyl or benzyl; and $R^2$ is hydrogen; and $R^3$ is $C_{1-6}$-alkyl optionally substituted with one, two or three fluorine atoms or cyano, $C_{2-6}$-alkenyl optionally substituted with one, two or three fluorine atoms, $C_{2-6}$-alkynyl optionally substituted with one, two or three fluorine atoms, $C_{3-7}$-cycloalkyl, phenyl or benzyl wherein each aromatic group is optionally substituted with halogen, $C_{1-4}$-alkyl, $-NO^2$, $-CN$, $-CF_3$ or $-OR^6$ wherein $R^6$ is hydrogen, $C_{1-3}$-alkyl, $C_{2-4}$-alkenyl, $C_{2-4}$-alkynyl or $C_{3-4}$-cycloalkyl, or $R^2$ and $R^3$ form together with the nitrogen atom a three, four, five, six or seven membered saturated or unsaturated heterocyclic ring; and $R^4$ is hydrogen, halogen, $C_{1-6}$-alkyl optionally substituted by one, two or three fluorine atoms, $C_{2-6}$-alkenyl optionally substituted by one, two or three fluorine atoms, $C_{2-6}$-alkynyl optionally substituted by one, two or three fluorine atoms, $C_{3-7}$-cycloalkyl, $-OR^5$ or $-SR^5$ wherein $R^5$ is $C_{1-6}$-alkyl, $C_{2-6}$-alkenyl or $C_{2-6}$-alkynyl each of which is optionally substituted with one, two or three fluorine atoms; or a pharmaceutically acceptable salt thereof.

* * * * *